US010022507B2

(12) United States Patent
Cassidy

(10) Patent No.: US 10,022,507 B2
(45) Date of Patent: *Jul. 17, 2018

(54) INTRAVENOUS FLUID WARMING SYSTEM

(71) Applicant: Vital Signs, Inc., Totowa, NJ (US)

(72) Inventor: David E. Cassidy, Chelmsford, MA (US)

(73) Assignee: VITAL SIGNS, INC.

( * ) Notice: Subject to any disclaimer, the term of this patent is extended or adjusted under 35 U.S.C. 154(b) by 574 days.

This patent is subject to a terminal disclaimer.

(21) Appl. No.: 14/188,473

(22) Filed: Feb. 24, 2014

(65) Prior Publication Data

US 2014/0169775 A1 Jun. 19, 2014

Related U.S. Application Data

(60) Continuation of application No. 13/438,294, filed on Apr. 3, 2012, now Pat. No. 8,660,415, which is a
(Continued)

(51) Int. Cl.
  *A61F 7/00* (2006.01)
  *F24H 1/10* (2006.01)
  *A61M 5/44* (2006.01)

(52) U.S. Cl.
  CPC ....... *A61M 5/44* (2013.01); *A61M 2205/3653* (2013.01); *A61M 2205/583* (2013.01)

(58) Field of Classification Search
  CPC ................... A61M 5/44; A61M 5/445; A61M 2205/3372; A61M 2205/3368;
(Continued)

(56) References Cited

U.S. PATENT DOCUMENTS 3,443,060 A 5/1969 Smith
3,590,215 A 6/1971 Anderson et al.
(Continued)

FOREIGN PATENT DOCUMENTS

DE 3731189 A1 4/1988
JP 63122462 5/1988
(Continued)

OTHER PUBLICATIONS

Unofficial translation of JPO Office action from JP App. No. 2011-288194 dated Jan. 22, 2013.
(Continued)

*Primary Examiner* — Tu B Hoang
*Assistant Examiner* — Alba Rosario-Aponte
(74) *Attorney, Agent, or Firm* — McDermott Will & Emery LLP

(57) ABSTRACT

A fluid warming device may include a housing comprising a main body, a heat exchange body receiving compartment, and a cover movably coupled to the main body between an open position and a closed position; a heater assembly disposed within the main body and having a heat conducting surface disposed proximate the heat exchange body receiving compartment; and a heat exchange body removably disposable in the heat exchange body receiving compartment of the main body and having an input port and an output port to couple the heat exchange body to tubing to flow a fluid to be warmed through the heat exchange body. In another aspect, a fluid warming system increases or decreases power to a heater assembly to adjust the fluid temperature to ensure that the fluid is at an appropriate temperature when it reaches the patient.

13 Claims, 10 Drawing Sheets

Related U.S. Application Data continuation of application No. 12/983,420, filed on Jan. 3, 2011, now Pat. No. 8,150,244, which is a division of application No. 11/385,085, filed on Mar. 21, 2006, now Pat. No. 7,865,072.

(60) Provisional application No. 60/663,857, filed on Mar. 21, 2005.

(58) Field of Classification Search
CPC .... A61M 2205/3653; A61M 2205/583; A61M 2205/8212; A61M 2205/8206
USPC ............... 392/470, 465, 484, 494, 479, 485; 604/113, 114, 111, 93.01; 165/253, 165/287–293
See application file for complete search history.

(56) References Cited

U.S. PATENT DOCUMENTS

| | | | |
|---|---|---|---|
| 4,019,020 A | | 4/1977 | Bilbee et al. |
| 4,293,762 A | | 10/1981 | Ogawa |
| 4,464,563 A | | 8/1984 | Jewett |
| 4,680,445 A | | 7/1987 | Ogawa |
| 4,735,609 A | * | 4/1988 | Comeau ............... A61M 5/44 165/170 |
| 4,847,470 A | | 7/1989 | Bakke |
| 4,894,164 A | | 1/1990 | Polaschegg |
| 4,906,816 A | | 3/1990 | Van Leerdam |
| 5,250,032 A | * | 10/1993 | Carter, Jr. ............... A61M 5/44 219/535 |
| 5,319,170 A | | 6/1994 | Cassidy |
| 5,420,962 A | | 5/1995 | Bakke |
| 6,047,108 A | | 4/2000 | Sword et al. |
| 6,096,007 A | | 8/2000 | Haan et al. |
| 6,175,688 B1 | * | 1/2001 | Cassidy ............... A61M 5/44 392/470 |
| 6,336,003 B1 | * | 1/2002 | Mitsunaga ............... A61M 5/44 392/470 |
| 6,423,268 B1 | | 7/2002 | King et al. |
| 6,480,257 B2 | | 11/2002 | Cassidy et al. |
| 6,535,689 B2 | | 3/2003 | Augustine et al. |
| 6,643,454 B1 | | 11/2003 | Rochelle |
| 6,722,782 B2 | | 4/2004 | Faries, Jr. et al. |
| 6,788,885 B2 | | 9/2004 | Mitsunaga et al. |
| 7,163,031 B2 | * | 1/2007 | Graves .................... G21F 5/015 141/104 |
| 7,289,724 B2 | | 10/2007 | Fürnrohr et al. |
| 7,865,072 B2 | * | 1/2011 | Cassidy .................. A61M 5/44 392/470 |
| 8,150,244 B2 | * | 4/2012 | Cassidy .................. A61M 5/44 392/470 |
| 2001/0009610 A1 | * | 7/2001 | Augustine ............... A61M 5/44 392/470 |
| 2002/0021741 A1 | | 2/2002 | Faries et al. |
| 2002/0081109 A1 | * | 6/2002 | Mitsunaga .............. A61M 5/44 392/470 |
| 2002/0181948 A1 | | 12/2002 | Akahane |
| 2003/0114795 A1 | * | 6/2003 | Faries, Jr. ............... A61M 5/44 604/113 |
| 2004/0190885 A1 | | 9/2004 | Entenman et al. |
| 2004/0247016 A1 | | 12/2004 | Faries et al. |
| 2005/0008354 A1 | | 1/2005 | Cassidy |
| 2006/0153549 A1 | | 7/2006 | Cazzini et al. |

FOREIGN PATENT DOCUMENTS

| | | |
|---|---|---|
| WO | WO-9838953 A1 | 9/1998 |
| WO | WO 2000/002608 | 1/2000 |
| WO | WO 2000/047252 | 8/2000 |
| WO | WO-0053246 A1 | 9/2000 |
| WO | WO 2005/009500 | 2/2005 |

OTHER PUBLICATIONS

Supplementary European Search Report in European Patent Application No. 06739047.6 dated Jul. 29, 2014, 9 pgs.

Extended European Search Report in European Patent Application No. 06748484.0 dated Oct. 24, 2014, 7 pgs.

Japanese Office Action for Application No. 2014-080966, dated Nov. 8, 2016, 5 pages excluding English translation.

European Office Action for Application No. 06739047.6, dated Oct. 16, 2017, 6 pages.

European Office Action for Application No. 06739047.6, dated Apr. 23, 2018, 5 pages.

* cited by examiner

INTRAVENOUS FLUID WARMING SYSTEM

CROSS-REFERENCE TO RELATED APPLICATIONS

This application is a continuation of co-pending U.S. patent application Ser. No. 13/438,294, filed on Apr. 3, 2012, which is a continuation of U.S. Pat. No. 8,150,244, filed on Jan. 3, 2011, which is a divisional of U.S. Pat. No. 7,865,072, filed on Mar. 21, 2006, which claims benefit of U.S. Provisional Patent Application Ser. No. 60/663,857, filed on Mar. 21, 2005. Each of the aforementioned related patent applications is herein incorporated by reference.

BACKGROUND

Intravenous (IV) fluid warming devices are known that heat an IV fluid prior to introducing the fluid into a patient. Warmed IV fluids that are administered at very low flow rates can cool as they flow down the IV tubing to the patient. Often this heat loss is ignored. One prior art approach has been to simply heat the fluid to 41 degrees C. to try to overcome the loss for all flow rates.

In another aspect of fluid warming, most IV fluid warmers heat fluid through flexible plastic walls. Because these walls are inefficient in transferring heat, heaters are exposed to both sides of the disposable set. This requires inserting the disposable set into a slot or hinged clam shell configuration. Both of these designs do not allow the user to see the fluid passing through the heat exchanger. As these plastic walls are flexible, the pressure necessary for good heat transfer cannot be guaranteed as it is supplied only by the gravitational force of the IV fluid bag height. Cleaning of configurations with slots is difficult and typically requires special tools or even disassembly, such as in the case of blood spills.

One type of exemplary medical fluid warming system is described in U.S. Pat. No. 7,158,719, the disclosure of which is incorporated by reference herein. In this device, fluid passes along a generally serpentine fluid flow path through a removable/disposable heat exchange body. The heat exchange body is in thermal contact with a resistive film heater via thermally conductive layers interposed between the heat exchange body and the heater. Temperature sensors are provided that sense the temperature of the heat exchange body and of the heater.

SUMMARY OF THE INVENTION

In some embodiments, a fluid warming device may include a housing comprising a main body, a heat exchange body receiving compartment, and a cover movably coupled to the main body between an open position and a closed position; a heater assembly disposed within the main body and having a heat conducting surface disposed proximate the heat exchange body receiving compartment; and a heat exchange body removably disposable in the heat exchange body receiving compartment of the main body and having an input port and an output port to couple the heat exchange body to tubing to flow a fluid to be warmed through the heat exchange body.

In some embodiments, a method of minimizing heat loss through IV tubing to a patient may include a) determining a temperature drop across a heat exchange body of an IV fluid warming device; b) determining a temperature drop of the IV tubing to the environment, the IV tubing extending from the IV fluid warming device to the patient; c) determining if the temperature drop along the IV tubing is greater than a determined temperature limit; d) determining if the total temperature drop along the IV tubing and across the heat exchange body is greater than a determined drop limit; e) if the determined values from c) or d) are greater than their respective limits, determining the actual fluid temperature as a fluid output temperature minus the drop limit; f) if either of the determined values from c) or d) are not greater than their respective limits, determining the actual fluid temperature as a fluid output temperature minus the heat exchanger temperature drop; and g) adjusting power to the heat exchanger to achieve a desired output temperature.

In some embodiments a method of minimizing heat loss through IV tubing to a patient may include a) providing a heat exchange body, coupled between an IV fluid source and the patient via IV tubing, to a heat exchange body receiving compartment of an IV fluid warming device that comprises a housing including a main body, the heat exchange body receiving compartment, a cover movably coupled to the main body between an open position and a closed position, and a heater assembly disposed within the main body and having a heat conducting surface disposed proximate the heat exchange body receiving compartment such that the heat exchange body is in heat exchange communication with the heater assembly; b) determining a temperature drop across the heat exchange body by dividing heater power of the heater assembly by the thermal resistance of the heater assembly; c) determining a temperature drop of the IV tubing to the environment, the IV tubing extending from the IV fluid warming device to the patient, by determining the difference between a fluid target temperature and ambient temperature, multiplying this difference by a radiation loss constant to get a result, and dividing the result by heater power of the heater assembly; d) determining if the temperature drop along the IV tubing is greater than a determined temperature limit; e) determining if the total temperature drop along the IV tubing and across the heat exchange body is greater than a determined drop limit; f) if the determined values from d) or e) are greater than their respective limits, determining the actual fluid temperature as a fluid output temperature minus the drop limit; g) if either of the determined values from d) or e) are not greater than their respective limits, determining the actual fluid temperature as a fluid output temperature minus the heat exchanger temperature drop; and h) adjusting power to the heat exchanger to achieve a desired output temperature.

BRIEF DESCRIPTION OF THE DRAWINGS

The invention will be more fully understood from the following detailed description taken in conjunction with the accompanying drawings in which.

DETAILED DESCRIPTION

Figure 1:
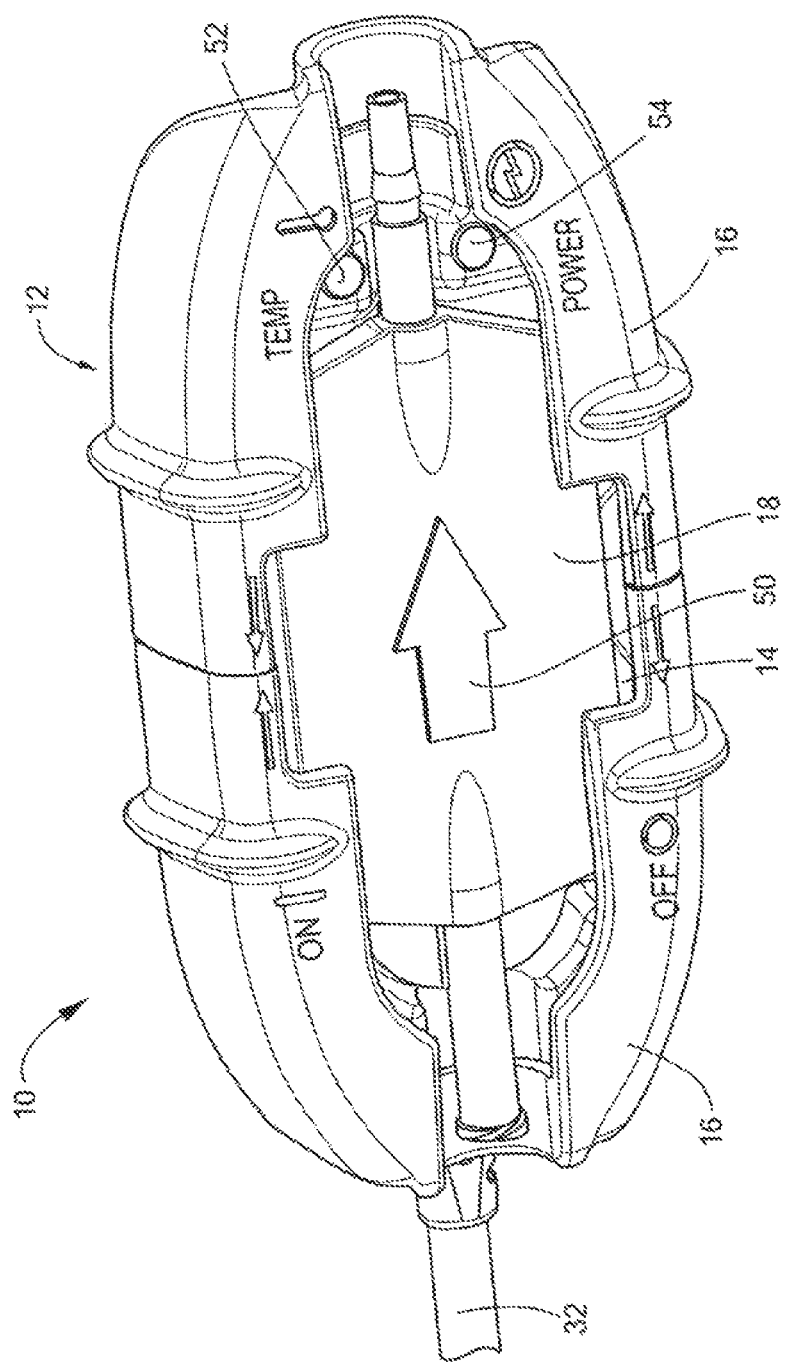
FIG. 1 is an isometric view of a fluid warming device illustrating slidable covers in a closed position according to the present invention.
Figure 2:
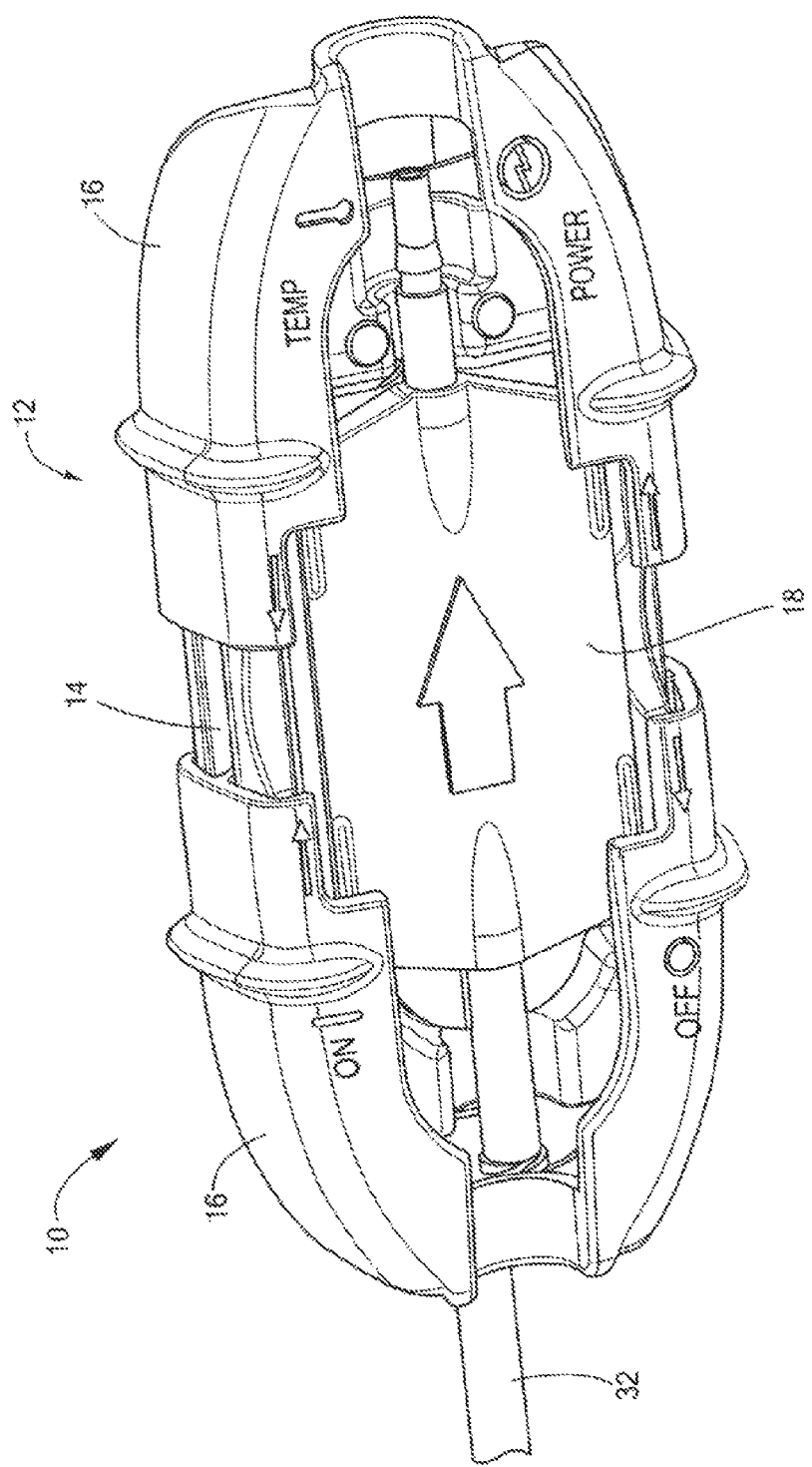
FIG. 2 is an isometric view of the fluid warming device of FIG. 1 illustrating the slidable covers in a half closed position.

A fluid warming device or warmer 10 according to the present invention is illustrated in FIGS. 1-7. The fluid warming device 10 includes a housing 12 having a main body 14 and two sliding or slidable covers 16. Within the housing 12, supported by the main body, are a removable heat exchange body 18 and a heating or heater assembly 20. The sliding covers 16 are independently slidable to a closed position in which they retain the removable heat exchange body 18 in place, as described more fully below. The slidable covers 16 are preferably identical.

Figure 7:
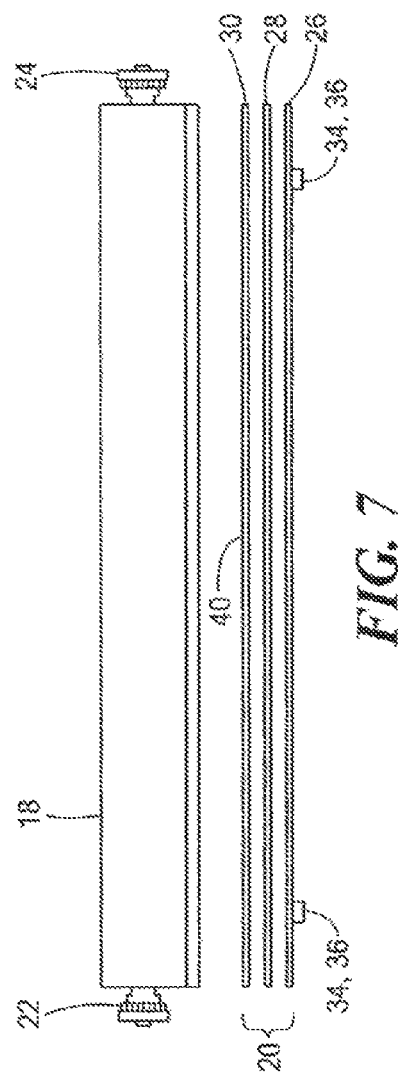
FIG. 7 is a schematic view of a disposable set and heater assembly of the fluid warming device of FIG. 1.

The removable heat exchange body 18 and the heating assembly 20 are illustrated schematically in FIG. 7. The heat exchange body, also called a disposable or removable set, includes an input port or connector 22 connectable to an IV tubing line from a source of IV fluid, which may include an infusion pump. The disposable set also includes an output port or connector 24 connectable to a further IV tubing line to deliver the IV fluid to the patient. Within the disposable set, the IV fluid flows along a flow path (not shown) having a serpentine or other suitable configuration between the input and output ports to optimize heat transfer to the fluid. See, for example, U.S. Pat. No. 7,158,719. The disposable set 18 is formed from any suitable material, such as aluminum, to facilitate heat transfer to the fluid flowing therein. When inserted in the housing 12 with the sliding covers 16 in a closed position, the disposable set 18 is held in thermal contact with the heater assembly 20, so that heat transfer from the heater assembly 20 to the disposable set 18 causes heating of an IV fluid flowing therethrough.

Figure 3:
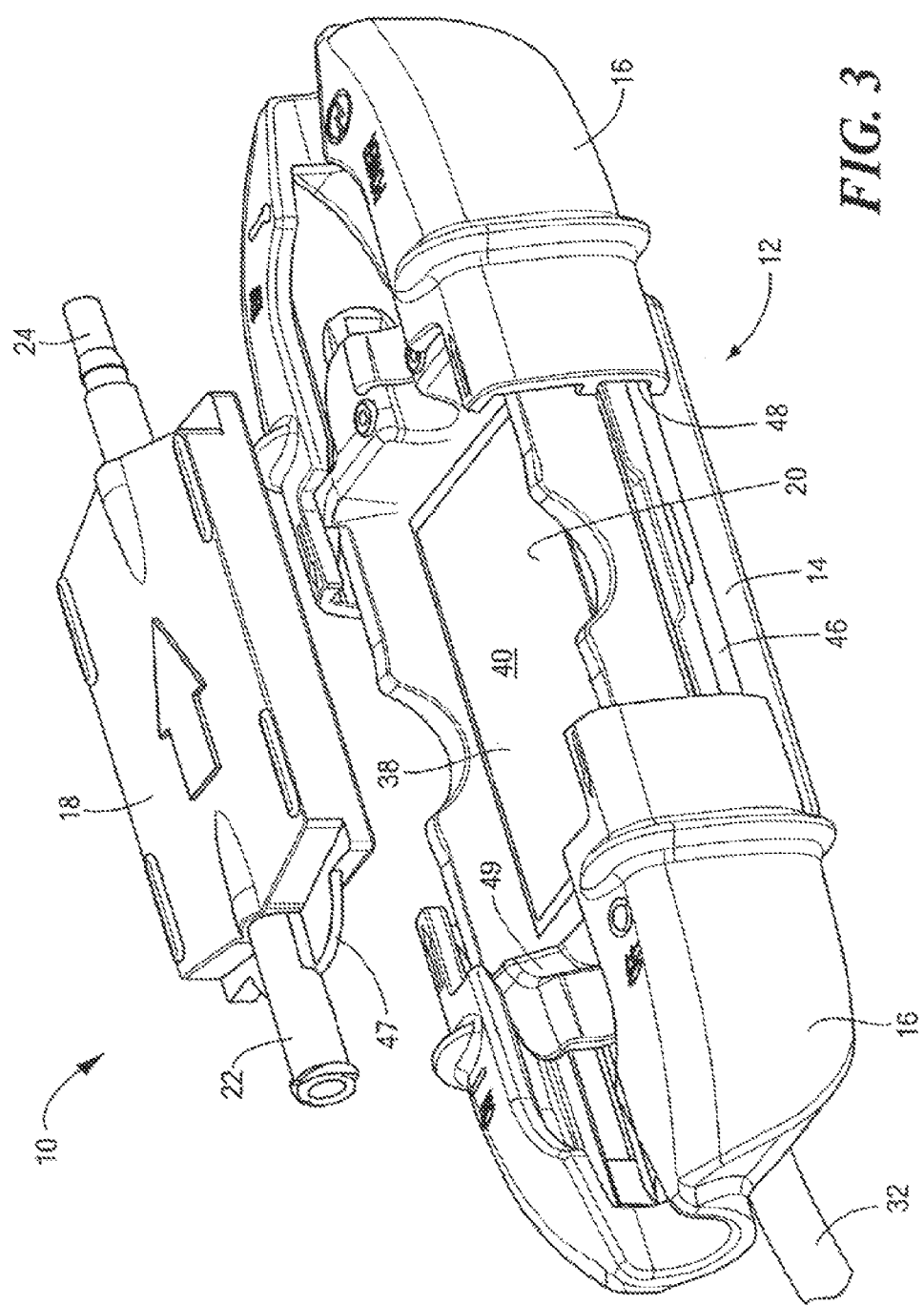
FIG. 3 is an isometric exploded view of the fluid warming device of FIG. 1 with the slidable covers in an open position and a disposable set removed.

The heater assembly 20 is affixed within the main body 14 of the housing 12. The heater assembly 20 includes a heater 26 and one or more thermally conductive layers 28, 30 interposed between the disposable set 18 and the heater 26. Preferably, the heater 26 is an electrically powered resistive thin film heater. A power line 32 to the heater from a suitable power source is provided. Alternatively, the device may include a battery compartment or a connection to a battery pack, for example, for portable operation. Temperature sensors 34, 36 are provided that sense the temperature of the disposable set 18 and of the heater 26. See, for example, U.S. Pat. No. 7,158,719. The thermally conductive layers also electrically insulate the disposable set from the resistive heater 26. One thermally conductive layer 28 may suitably comprise a phase transition material, and the other thermally conductive layer 30 may suitably comprise a material such as a graphite to optimize heat transfer between the heater and the disposable set. See, for example, U.S. Pat. No. 7,158,719. It will be appreciated that other or further thermally conductive layers may be provided. As seen in FIGS. 3 and 7, the main body 14 includes a compartment 38 on one side to receive the disposable set 18 in contact with an exposed surface 40 of the uppermost thermally conductive layer 30.

Figure 4:
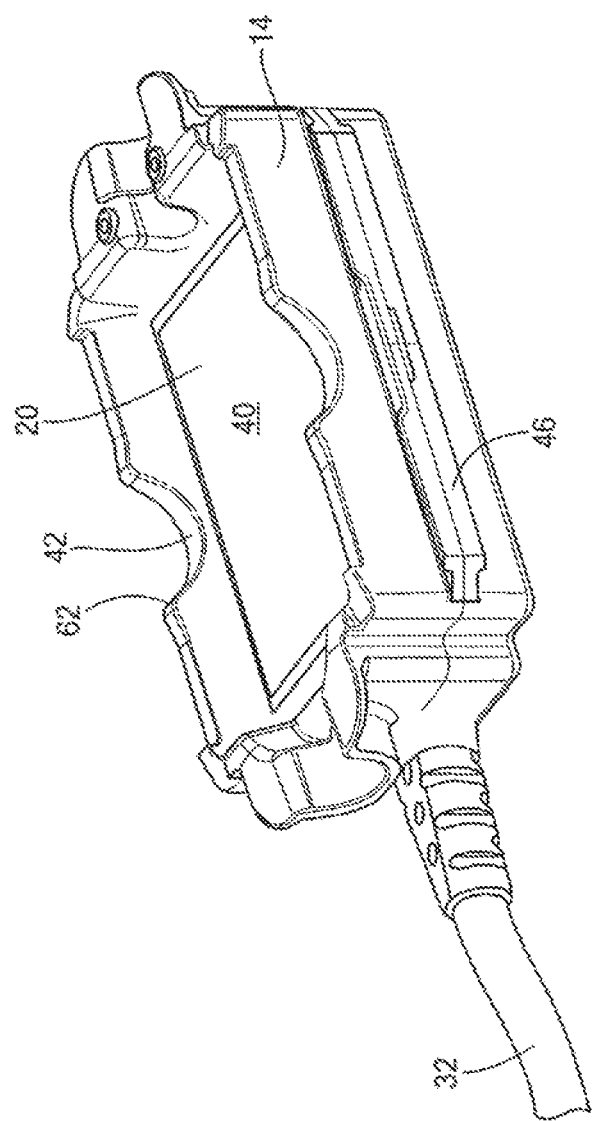
FIG. 4 is an isometric view of a main body of the housing of the device of FIG. 1 with the slidable covers fully removed.

As noted above, the heat exchange body or disposable set 18 is removable from the housing 12. The disposable set 18 can be removed from the main body 14 of the housing 12 by sliding the two opposed sliding covers 16 outwardly in opposite directions. In this manner, the removable set 18 can be lifted out of the housing 12 with the IV tubing still attached to the input and output connectors 22, 24, without breaking the fluid path. Finger cutouts 42 may be provided for ease of grasping the disposable set 18 in the main body 14, as seen in FIG. 4.

Any suitable sliding mechanism to allow the covers 16 to move axially into the closed position can be provided. In the embodiment shown in FIG. 4, the main body 14 of the housing 12 includes protruding longitudinal tracks 46 along two opposed longitudinal outer wall surfaces of the main body 14. See also FIG. 5. The sliding covers 16 include complementary longitudinal recesses 48 along inner wall surfaces that mate with the tracks 46 and allow the covers to slide axially along the main body, as seen in FIG. 3. When in the closed position, the sliding covers 16 extend over the edges of the disposable set 18 within the recess 48 of the main body, thereby retaining the disposable set therein. See FIG. 1. The covers 16 also compress the disposable set 18 to the outermost thermally conducting surface 40 of the heater assembly. This compression provides the necessary pressure for proper heat transfer between the heater assembly 20 and the disposable set 18. Preferably, the covers 16 are retained in the closed position by frictional engagement with the disposable set 18. Alternatively, any suitable latching or retaining mechanism may be provided.

Also, the covers 16 do not block the view of the bulk of the mid portion of the disposable set 18, allowing the operator to view the fluid passing through the disposable set. The disposable set 18 is also keyed to the main body 14 in any suitable manner so that it fits within the compartment 38 in the correct orientation. For example, in FIG. 3, one end 47 of the disposable set 18 may be rounded to fit within a correspondingly rounded portion 49 of the compartment 38. The disposable set 18 may include an arrow 50 thereon, seen in FIG. 1, to provide an indication of the direction of flow, so that the disposable set 18 is inserted in the housing 12 in the correct orientation. The covers 16 do not block this arrow. Also, the main body 14 preferably includes indicator lights, such as LEDs, thereon. For example, one LED 52 may provide an indication of temperature at the output port 24, and another LED 54 may provide an indication that the heater 26 is connected to the power source. The covers 16 do not block these indicator lights 52, 54 either.

In one embodiment, the covers 16 can be maintained in two positions on the main body 14 or can be removed fully from the main body 14. While on the main body 14, the covers 16 can be in a fully closed position, as in FIG. 1, or an open position, as in FIG. 3. The covers 16 can include magnets or Hall Effect devices or other proximity sensors that interface with a corresponding component within the main body 14 to determine the positions of the covers and cause operation of any appropriate switches. In a further embodiment, the covers 16 can be maintained in a third or intermediate, half closed, position on the main body 14, described further below.

More particularly, in the fully closed position, (see FIG. 1), the covers 16 apply full pressure to the disposable set 18 to ensure good thermal contact with the heater assembly 20. In this position, the sliding covers 16 can also be used to turn the power on to commence warming and/or to activate any audible or visible alarm(s). In the half closed position (see FIG. 2), the disposable set 18 is still held in place by the covers 16, but warming is stopped, the audible alarm is silenced, and the visual indicators 52, 54 are turned off. The status LED 54 could be flashed in battery operation to inform the user that the warmer is connected to the battery and draining When the covers 16 are in the open position (see FIG. 3), the disposable set 18 can be inserted and removed. No heating takes place, the audible alarm is silenced, and visual indicators 52, 54 are turned off. The status LED 54 could be flashed in battery operation to inform the user that the heater is 26 connected to the battery and draining.

Figure 5:
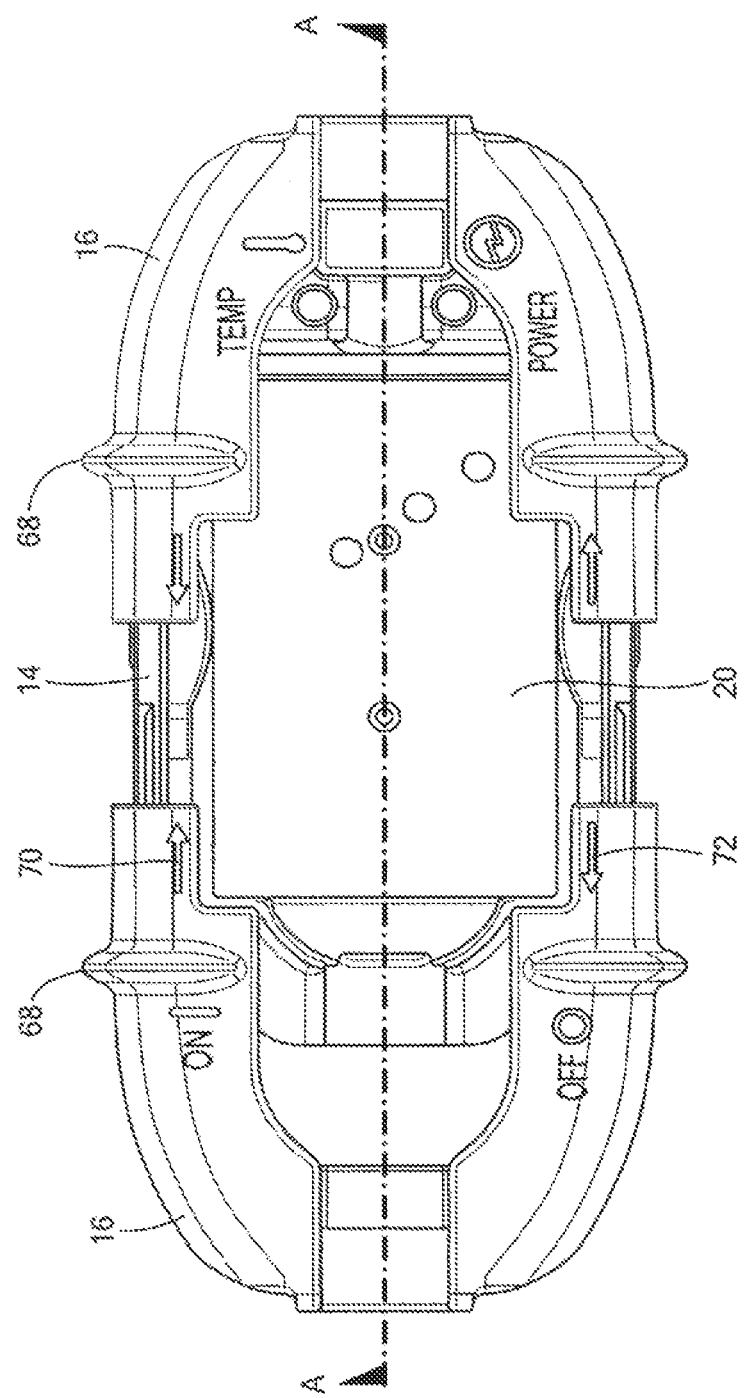
FIG. 5 is a plan view of the device of FIG. 2.
Figure 6:
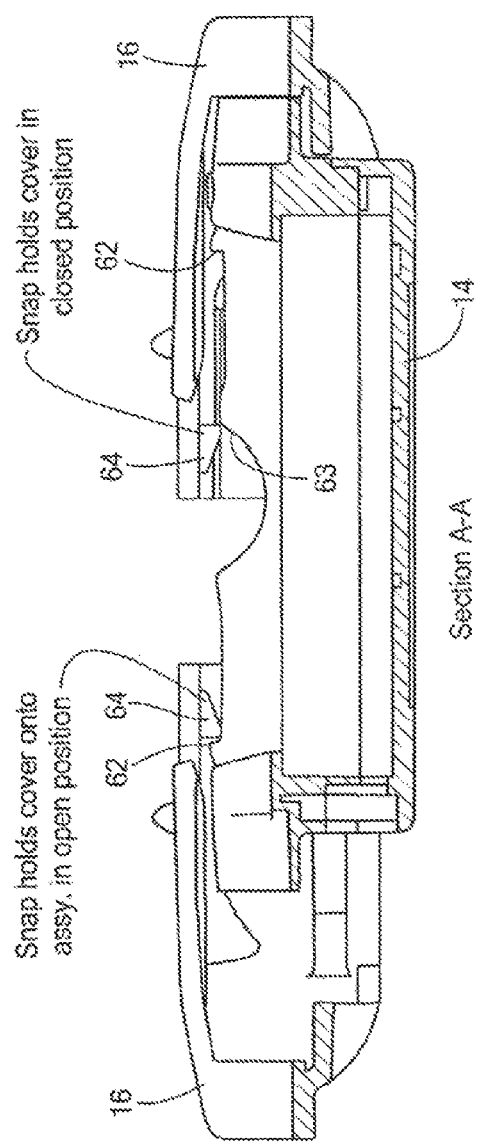
FIG. 6 is a cross sectional view taken along line A-A of FIG. 5.

Any suitable latching or retaining mechanism can be provided to retain the covers 16 in the desired positions relative to the main body 14. For example, as shown in FIGS. 5 and 6, recessed surfaces 62 are provided on the main body 14 that latch with corresponding tabs 64 on the covers 16 in the open position, preventing the covers 16 from readily coming off the main body 14. Also, the tabs 64 abut surfaces 63 to hold the covers 16 in the closed position. Finger grips 68 are provided to aid in grasping the covers 16 to push or pull them to the desired position. The closed (and power on) position can be indicated by arrows 70 and an adjacent "ON" marking on the covers. Similarly, the open (and power off) position can be indicated by arrows 72 and an adjacent "OFF" marking on the covers 16. The covers 16 can be fully removed from the main body 14 in any suitable manner, for example, by the insertion of a suitable tool, such as a screw driver or dime, to lift the tab 64 over the surfaces 62. Alternatively, a latching or retaining mechanism can be configured to release simply by the use of sufficient force. Removal of the covers 16 allows the device to be readily cleaned. Alternatively, passageways in the interior surfaces of the covers 16 and a water tight main body housing allow cold sterilization by dipping in a sterilization fluid without complete removal of the covers 16.

Figure 8:
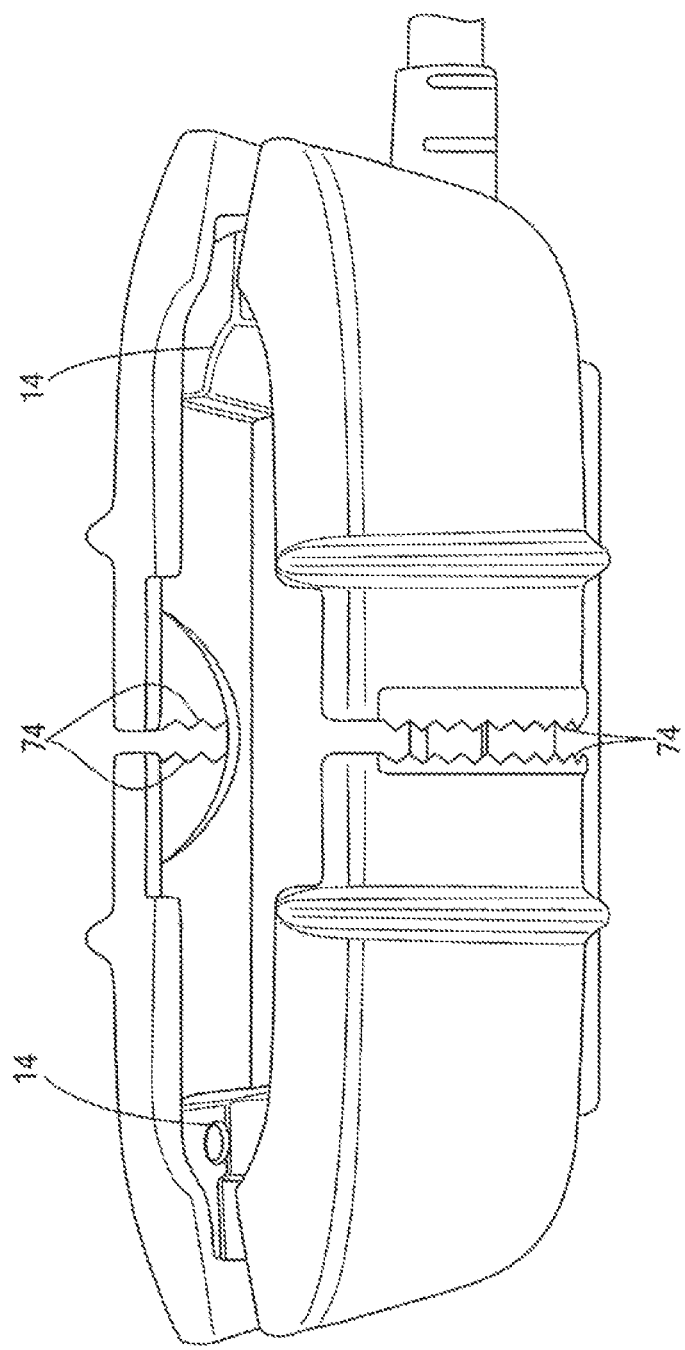
FIG. 8 is a side view of a further embodiment of a fluid warming device illustrating gripping faces on the slidable covers.

Referring to FIG. 8, the sliding covers 14 may include opposed faces 74 that include gripping teeth thereon to form gripping faces. The gripping faces can be used to grip hospital clothing or bedding and hold the warmer 10 in place to reduce stress on the IV line when the covers are fully closed.

In another aspect of the present invention, power to the heater 26 can be increased or decreased to adjust the fluid temperature to ensure that the fluid is at an appropriate temperature when it reaches the patient. More particularly, some IV fluids that have been warmed are administered at very low flow rates. These fluids cool as they travel down the IV tubing to the patient. The greater the difference between ambient temperature and the fluid temperature, the greater the radiated heat losses from the IV tubing.

A suitable controller is provided to perform the calculations and communicate with the heater 26 to make the desired adjustments. Heater power is determined by the difference between a target temperature (typically in the range of 39 to 41 degrees C.), and the actual fluid temperature.

Figure 9:
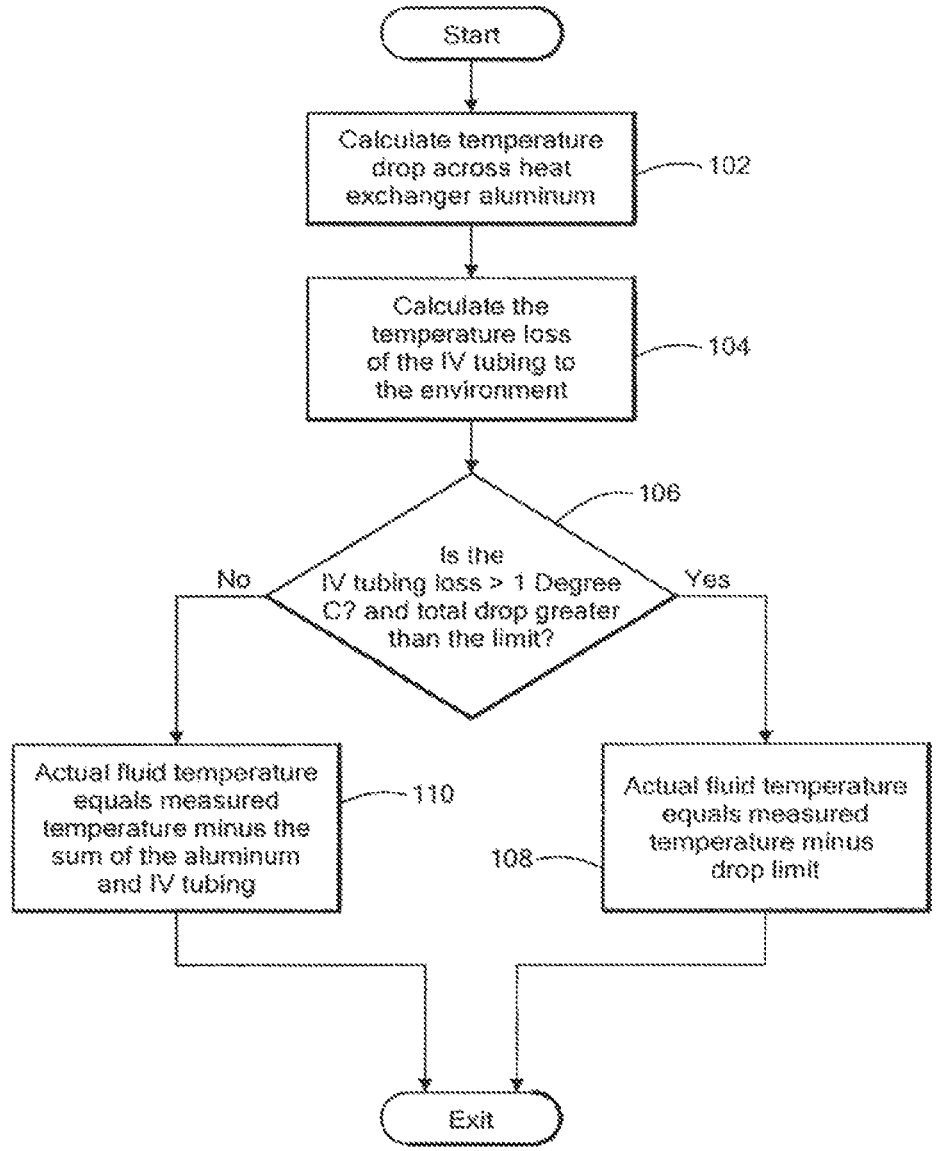
FIG. 9 is a flow chart illustrating a system for adjusting power to a heater of a fluid warming device to accommodate heat loss in an IV tubing at low flow rates.
Figure 10:
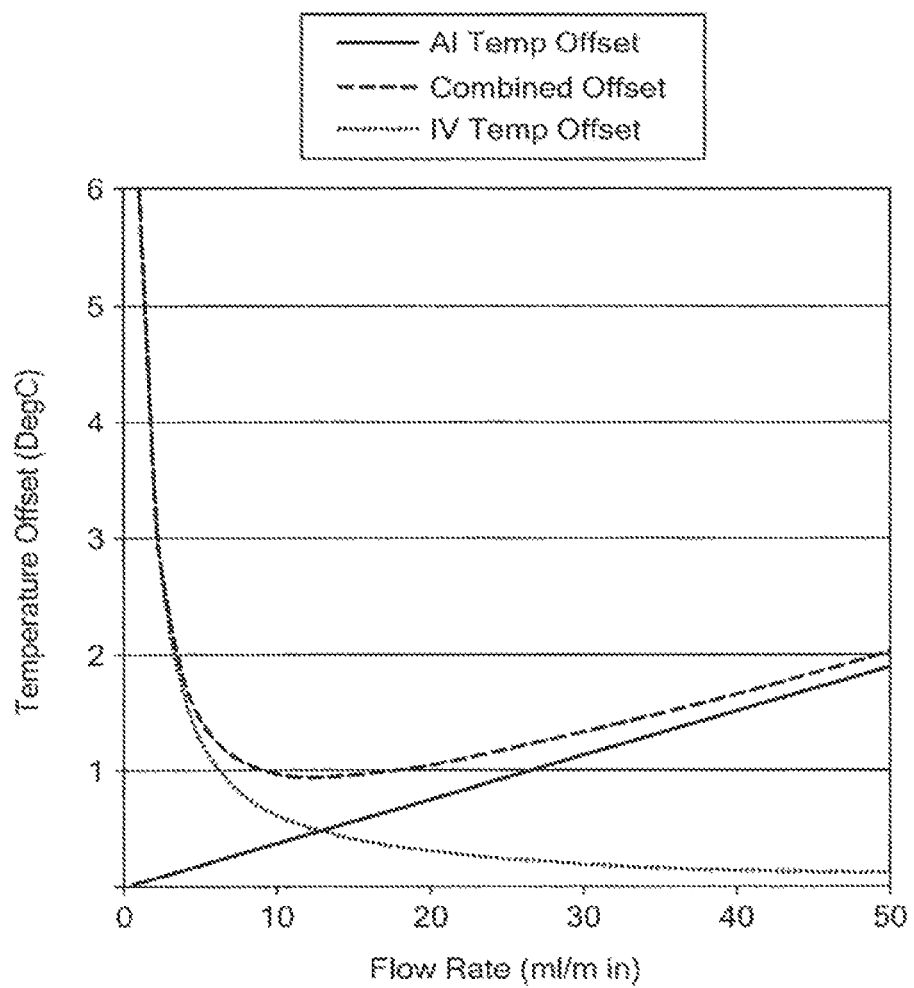
FIG. 10 is a graph illustrating heat loss across a disposable set heat exchange body and along a length of IV tubing and their combined heat losses.

Referring to FIG. 9, the temperature drop across the heat exchanger is calculated (step 102). This temperature drop is equal to the heater power divided by the thermal resistance of the heater assembly 20. The thermal resistance can be readily determined by one of skill in the art from the thickness, thermal conductivity and area of the materials between the heater 26 and the fluid and stored as a constant.

Figure 11:
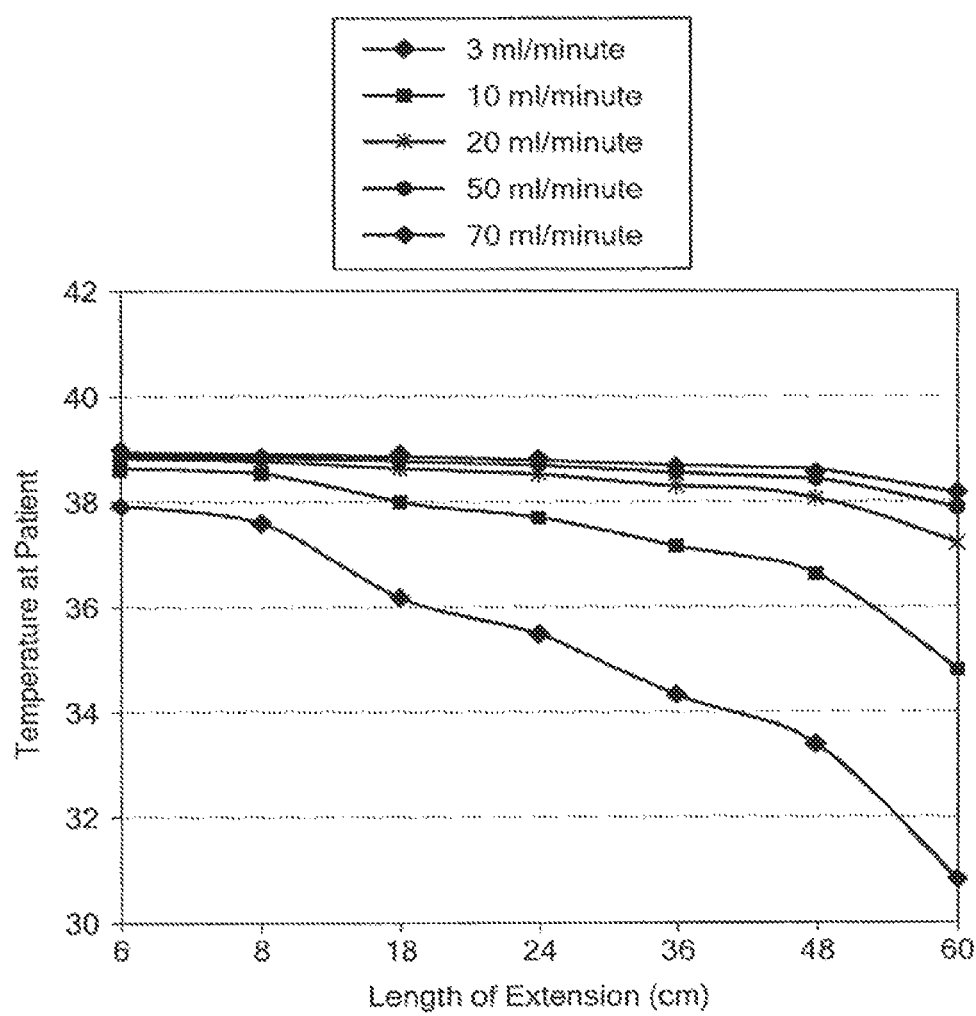
FIG. 11 is a graph illustrating temperature loss for various lengths of IV tubing and various flow rates.

Then, the controller calculates the temperature loss of the IV tubing to the environment (step 104). First, the difference between the fluid target temperature and the ambient temperature is determined. The temperature loss is equal to this temperature difference multiplied by the radiation loss and divided by the heater power. The ambient temperature is measured by a suitable sensor located within the warming device 10 in close contact with the housing, which is very close to ambient temperature. The radiation loss is a constant that is derived from experimentation with various lengths of the IV tubing and various flow rates. See FIG. 11.

Next, at step 106, the controller determines if the IV tubing loss is greater than 1 degree C. Also at step 106, the controller also determines if the total drop along the IV tubing and across the heat exchanger 18 is greater than a drop limit. The drop limit is the maximum temperature that the fluid can be artificially raised so that the allowable surface temperature on the heat exchanger is not exceeded, for example, no greater than 3 degrees C. from the desired target temperature. If the answer at step 106 is Yes, the actual fluid temperature is calculated at step 108 as the measured fluid output temperature minus the drop limit. If the answer at step 106 is No, the actual fluid temperature is calculated at step 110 as the fluid output temperature in the IV tubing drop minus the IV tubing drop (from step 102) minus the heat exchanger drop (from step 104). Using the calculated value of the actual temperature, heater power is adjusted appropriately.

In this manner, heat loss along the IV tubing can be more efficiently controlled. The system allows the fluid warming device 10 to be located a bit farther from the infusion site and still deliver normothermic fluid.

The invention is not to be limited by what has been particularly shown and described, except as indicated by the appended claims.

What is claimed is:

1. A fluid warming device, comprising:
    a heat exchange body configured to conduct fluid from an input port to an output port;
    a housing having a main body with a recess that is configured to removably receive the heat exchange body, the housing further comprising a pair of axially slidable covers having a closed position in which the pair of axially slidable covers retain the heat exchange body within the recess, wherein, in the closed position, open portions of the pair of axially slidable covers provide a view of a fluid flow through a mid portion of the heat exchange body, and wherein the axially slidable covers are slidable, along longitudinal tracks on the main body, outwardly in opposite directions to an open position for receiving and removal of the heat exchange body from the housing;
    a heater assembly, having a temperature sensor, disposed within the housing, the heater assembly configured to transfer heat to the heat exchange body; and
    a controller configured to adjust a heater power of the heater.

2. The fluid warming device of claim 1, further comprising a fluid line connected to the output port.

3. The fluid warming device of claim 2, wherein the housing further comprises a hollow portion around the output port, such that the heat exchange body is removable without disconnecting the fluid line.

4. The fluid warming device of claim 1, wherein at least one of the slidable covers includes a hollow portion for exposing at least the output port.

5. The fluid warming device of claim 1, wherein at least one of the slidable covers includes gripping teeth.

6. A fluid warming device, comprising:

a heat exchange body configured to conduct fluid therethrough in one direction from an input port to an output port;

a housing configured to removably receive the heat exchange body;

a heater assembly disposed within the housing, the heater assembly configured to transfer heat to the heat exchange body;

a first axially slidable cover and a second axially slidable cover configured to hold the heat exchange body against the heater assembly when the first axially slidable cover and the second axially slidable cover are in a closed position in which an opening of each of the first axially slidable cover and the second axially slidable cover provides a view of a fluid flow through a mid portion of the heat exchange body, and wherein the axially slidable covers are slidable, along longitudinal tracks on the housing, outwardly in opposite directions to an open position for receiving and removal of the heat exchange body from the housing; and a controller that adjusts a heater power of the heater assembly.

7. The fluid warming device of claim 6, wherein the first slidable cover includes a first hollow portion for exposing the input port and the second slidable cover includes a second hollow portion for exposing the output port.

8. The fluid warming device of claim 6, wherein the first slidable cover includes a first face and the second slidable cover includes a second face, the first face touching the second face when the first and second slidable covers are fully closed.

9. The fluid warming device of claim 8, wherein the first and second faces include gripping teeth.

10. The fluid warming device of claim 6, further comprising a battery.

11. The fluid warming device of claim 10, wherein the heater assembly is powered by the battery when the first and second slidable covers are fully closed.

12. The fluid warming device of claim 10, further comprising a visual indicator for indicating a status of the battery.

13. The fluid warming device of claim 6, further comprising a proximity sensor configured to determine positions of the first and second slidable covers.

* * * * *